United States Patent
Ding et al.

(10) Patent No.: US 11,593,942 B2
(45) Date of Patent: Feb. 28, 2023

(54) FULLY CONVOLUTIONAL GENETIC NEURAL NETWORK METHOD FOR SEGMENTATION OF INFANT BRAIN RECORD IMAGES

(71) Applicant: NANTONG UNIVERSITY, Jiangsu (CN)

(72) Inventors: Weiping Ding, Jiangsu (CN); Zhihao Feng, Jiangsu (CN); Ming Li, Jiangsu (CN); Ying Sun, Jiangsu (CN); Yi Zhang, Jiangsu (CN); Hengrong Ju, Jiangsu (CN); Jinxin Cao, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 17/620,756

(22) PCT Filed: Apr. 12, 2021

(86) PCT No.: PCT/CN2021/086438
§ 371 (c)(1),
(2) Date: Dec. 20, 2021

(87) PCT Pub. No.: WO2022/016912
PCT Pub. Date: Jan. 27, 2022

(65) Prior Publication Data
US 2022/0327705 A1  Oct. 13, 2022

(30) Foreign Application Priority Data

Jul. 20, 2020 (CN) .......................... 202010697178.1

(51) Int. Cl.
*G06T 7/00* (2017.01)
*G06T 7/10* (2017.01)
(Continued)

(52) U.S. Cl.
CPC .............. *G06T 7/0014* (2013.01); *G06T 7/10* (2017.01); *G06V 10/776* (2022.01); *G06V 10/82* (2022.01);
(Continued)

(58) Field of Classification Search
CPC ..................... G06T 7/0014; G06T 7/10; G06T 2207/20081; G06T 2207/20084;
(Continued)

(56) References Cited

U.S. PATENT DOCUMENTS 11,474,180 B2 * 10/2022 Wu ...................... A61B 5/4064
2019/0370970 A1 * 12/2019 Kim ...................... G06T 7/0016
(Continued)

FOREIGN PATENT DOCUMENTS

CN    108416783    8/2018
CN    110929775    3/2020
(Continued)

OTHER PUBLICATIONS

D. Nie, L. Wang, Y. Gao and D. Shen, "Fully convolutional networks for multi-modality isointense infant brain image segmentation," 2016 IEEE 13th International Symposium on Biomedical Imaging (ISBI), 2016, pp. 1342-1345, doi: 10.1109/ISBI.2016.7493515. (Year: 2016).*
(Continued)

*Primary Examiner* — Van D Huynh
(74) *Attorney, Agent, or Firm* — JCIP Global Inc.

(57) ABSTRACT

Disclosed is a fully convolutional genetic neural network method for segmentation of infant brain record images. First, infant brain record image data is input and preprocessed, and genetic coding initialization is performed for parameters according to the length of a DMPGA-FCN network weight. Then, m individuals are randomly grouped into genetic native subpopulations and corresponding twin (Continued)

subpopulations are derived, where respective crossover probability and mutation probability pm of all the subpopulations are determined from disjoint intervals; and an optimal initialization value fa is searched for by using a genetic operator. Afterwards, fa is used as a forward propagation calculation parameter and a weighting operation is performed on the feature address featuremap. Finally, a pixel-by-pixel cross-entropy loss is calculated between predicted infant brain record images and standard segmented images to reversely update the weights, thus finally obtaining optimal weights of a network model for segmentation of the infant brain record images.

3 Claims, 3 Drawing Sheets (51) Int. Cl.
G16H 30/40 (2018.01)
G06V 10/82 (2022.01)
G06V 10/776 (2022.01)

(52) U.S. Cl.
CPC ... *G16H 30/40* (2018.01); *G06T 2207/20081* (2013.01); *G06T 2207/20084* (2013.01); *G06T 2207/30016* (2013.01); *G06V 2201/031* (2022.01)

(58) Field of Classification Search
CPC .............. G06T 2207/30016; G06T 7/11; G06T 7/0012; G06V 10/776; G06V 10/82; G06V 2201/031; G16H 30/40; G06N 3/0454; G06N 3/08

USPC .......................................................... 382/128
See application file for complete search history.

(56) References Cited

U.S. PATENT DOCUMENTS

2020/0082507 A1* 3/2020 Fang ................... G06N 3/04
2020/0167930 A1* 5/2020 Wang .................. G06T 7/0012
2020/0380687 A1* 12/2020 Avital ................. A61B 5/0042

FOREIGN PATENT DOCUMENTS

| CN | 111259602 | 6/2020 |
| CN | 112001887 | 11/2020 |
| WO | 2020120238 | 6/2020 |

OTHER PUBLICATIONS

S. Kumar, S. Conjeti, A. G. Roy, C. Wachinger and N. Navab, "InfiNet: Fully convolutional networks for infant brain MRI segmentation," 2018 IEEE 15th International Symposium on Biomedical Imaging (ISBI 2018), 2018, pp. 145-148, doi: 10.1109/ISBI.2018.8363542. (Year: 2018).*

J. Bernal, K. Kushibar, M. Cabezas, S. Valverde, A. Oliver and X. Lladó, "Quantitative Analysis of Patch-Based Fully Convolutional Neural Networks for Tissue Segmentation on Brain Magnetic Resonance Imaging," in IEEE Access, vol. 7, pp. 89986-90002, 2019, doi: 10.1109/ACCESS.2019.2926697. (Year: 2019).*

"International Search Report (Form PCT/ISA/210) of PCT/CN2021/086438," dated Jul. 1, 2021, pp. 1-4.

"Written Opinion of the International Searching Authority (Form PCT/ISA/237) of PCT/CN2021/086438," dated Jul. 1, 2021, with English translation thereof, pp. 1-10.

* cited by examiner

FULLY CONVOLUTIONAL GENETIC NEURAL NETWORK METHOD FOR SEGMENTATION OF INFANT BRAIN RECORD IMAGES

CROSS-REFERENCE TO RELATED APPLICATION

This application is a 371 of international application of PCT application serial no. PCT/CN2021/086438, filed on Apr. 12, 2021, which claims the priority benefits of China Patent Application No. 202010697178.1, filed on Jul. 20, 2020. The entirety of each of the above-mentioned patent applications is hereby incorporated by reference herein and made a part of this specification.

TECHNICAL FIELD

The present disclosure relates to the intelligent processing field of medical image information, and more particularly, to a fully convolutional genetic neural network method for segmentation of infant brain record images.

BACKGROUND

Infancy is a critical period for brain development. During this period, the brain not only develops quickly, but also is highly malleable and has a much higher chance of suffering from various encephalopathy than adults or other growth periods. In recent years, the survival rate of high-risk and very-low-weight infants is significantly improved and the incidence of brain disease in infants is on the rise, resulting in great difficulty in early diagnosis. Therefore, active exploration of computer-aided early diagnosis of infant encephalopathy is of great significance to the diagnosis and evaluation of the infant encephalopathy.

With the rapid increase in the amount of annotated data and the huge improvement in the performance of the graphics processing unit in recent years, the research on fully convolutional neural network has risen rapidly, which has good advantages in the field of image segmentation applications. However, due to the features such as low resolution and grayscale non-uniformity of the infant brain record images, significant problems that the gradient descends, the algorithm tends to fall into the locally optimal solution, and the image feature information cannot be effectively retained easily occur during segmentation of the infant brain record images by using the conventional fully convolutional neural network methods, leading to problems such as time consuming, training difficulty, and low accuracy during segmentation of the infant brain record images with these methods, thus failing to acquire high-accuracy segmented infant brain record images.

SUMMARY

The present disclosure aims to provide a highly efficient and accurate fully convolutional genetic neural network method for segmentation of infant brain record images, which can greatly reduce the running time, and improve the accuracy of image segmentation, thus providing an important image feature basis for the clinical diagnosis and treatment of related infant brain diseases.

The present disclosure is implemented through the following technical solution:

A fully convolutional genetic neural network method for segmentation of infant brain record images specifically includes the following steps:

Step 1. inputting standard segmented images of the infant brain record images, and performing grayscale processing and enhancement processing for the infant brain record images; then, labeling the standard segmented infant brain record images by using an image labeling tool Image Labeler, where a training set is X=(x1, x2, . . . , xn), n=1, 2, 3, . . . ; and a label set is B=(b1, b2, . . . , bn), n=1, 2, 3, . . . ; and storing true values y_true of the labels corresponding to the infant brain record images;

Step 2. performing bilinear interpolation initialization f(i, j) for weight parameters of the fully convolutional genetic neural network used for the infant brain record images, where specific calculation is shown by the following formula (1):

$$f(i,j) = w_1 \times p_1 + w_2 \times p_2 + w_3 \times p_3 + w_4 \times p_4 \quad (1)$$

pi denoting the nearest four pixel points, i=1, 2, 3, 4; and wj denoting a corresponding weight of each point, j=1, 2, 3, 4; generating m individuals with a coding length of L by means of binary coding, where calculation of L is shown by the following formula (2):

$$L = F \times F \times D \times N \quad (2)$$

L being a coding length of the genetic individual, F being the size of a convolution kernel, N being the number of the convolution kernels, and D being the depth of a convolutional layer;

randomly assigning the individuals to a native subpopulation Pop, and deriving a twin population Pop' to generate an initial genetic evolution population, where values of a crossover probability pc and a mutation probability pm of the native population and its twin population are both selected from disjoint intervals (0,1/2) and [1/2,1); searching a feasible domain for optimal individuals by using a genetic operator, and conducting calculation by using the inter-class variance function as the fitness function f, where the calculation is shown by the following formula (3):

$$f = n_1 n_2 (G_{1k} - G_{2k})^2, \ k=1,2,3,\ldots n, \quad (3)$$

$n_1$ and $n_2$ respectively denoting the numbers of pixel points of the two foreground and background types in the infant brain record images, $G_{1k}$ denoting the gray level of the kth pixel point of the first type, and $G_{2k}$ denoting the gray level of the kth pixel point of the second type;

criticizing the superiority of the individuals according to the fitness function f and constantly updating the individuals in the population, till the genetic algorithm meets convergence conditions, to obtain globally optimal individuals fa; and using all the individuals in fa as initial weights of the fully convolutional genetic neural network for the infant brain record images;

Step 3. inputting the jth standard segmented infant brain record image in the training set to a forward propagation calculation model of the fully convolutional genetic neural network, and subjecting it to convolution cony, pooling pool, and deconvolution deconv calculation through multiple layers; and finally, conducting statistical calculation of the pixel-by-pixel classification probability, to output a predicted value matrix y_predict in the jth operation;

Step 4. conducting softmax calculation softmax (y_predict) by using a true value y_true$_{ij}$ and a predicted value y_predict$_{ij}$ in the mth operation, and calculating a pixel-by-pixel cross-entropy loss of the infant brain record images, to obtain a loss value loss$_m$ in the mth operation, where the calculation is shown by the following formula (4):

$$loss_m = -\Sigma_{class} y\_true_{ij} \log(y\_predict_{ij}) \quad (4)$$

y_true$_{ij}$ denoting a predicted value in the ith row and jth column of a pixel-by-pixel classification matrix, y_predict$_{ij}$ denoting a value in the ith row and jth column of the classification matrix of the standard segmented infant brain record images, and class denoting a total number of i×j pixels;

Step 5. performing callback of the network weights by returning the loos value and by means of a gradient descent algorithm, determining whether the network reaches end conditions, and if yes, using final network weights as the final trained weight parameters of the fully convolutional genetic neural network; and Step 6. introducing the final trained weight parameters into the network to form a fully convolutional genetic neural network model for segmentation of the infant brain record images;

then, inputting the infant brain record images, and subjecting the images to convolution cony, max-pooling max_pool, and deconvolution deconv calculation through multiple layers, to output segmented infant brain record images and further output pixel-by-pixel classification matrices y_ture.

As a further preferred solution of the fully convolutional genetic neural network method for segmentation of infant brain record images of the present disclosure, step 2 includes the following steps:

Step 2.1. establishing a forward propagation calculation model of the fully convolutional genetic neural network; randomly selecting a few infant brain record images from the training set of the standard segmented infant brain record images as reference images, and using the images left in the training set as a validation set; and repeatedly performing training and validation by means of cross validation;

Step 2.2. determining the number m of the genetic individuals, and performing bilinear interpolation initialization f(i, j) for the weight parameters of the fully convolutional genetic neural network, where the calculation is shown by the formula (1); and generating m individuals with a coding length of L by means of binary coding, where calculation of L is shown by the formula (2);

Step 2.3. randomly grouping all the individuals into native populations Pop, and deriving corresponding twin populations Pop', to finally form initial genetic evolution populations;

Step 2.4. selecting values of a crossover probability pc and a mutation probability pm of each pair of the native population Pop and its twin population Pop' from disjoint intervals, that is, randomly generating the respective crossover probability pc and mutation probability pm of all the populations within (0,1/2) and [1/2,1) respectively;

Step 2.5. selecting three optimal individuals with a certain probability from the original population to the new population by using a selection operator; and then selecting any two chromosomes from the population by using a crossover operator, and randomly selecting a gene locus according to the probability pc in exchange with each site in the chromosomes, where the calculation is shown by the following formula (5):

$$a_{mi} = a_{mi} \times (1-p_c) + a_{mi} \times p_c; \quad a_{ni} = a_{ni} \times (1-p_c) + a_{ni} \times p_c \quad (5)$$

a$_{mi}$ denoting the ith site of the mth chromosome, a$_{ni}$ denoting the ith site of the nth chromosome, and p$_c$ being the crossover probability; and afterwards, randomly selecting an individual from the population by using a mutation operator, and selecting a gene locus from the individual with the probability p$_m$ for mutation, to generate a more superior individual, where the calculation is shown by the following formula (6):

$$a_{mn} = a_{mn} + (a_{mn} - a_{max}) \times p_m \quad (6)$$

a$_{mn}$ denoting the nth site of the mth chromosome, a$_{max}$ denoting the upper genetic boundary, and p$_m$ being the mutation probability;

Step 2.6. replacing the worst individuals in the immigrant population with the optimal individuals in the emigrant population among the various populations by using a transfer operator, and then conducting calculation by using the inter-class variance function as the fitness function f, to criticize the superiority of the individuals, where the calculation is shown by the formula (3); and Step 2.7. determining whether a derived multi-population genetic algorithm (DMPGA) meets convergence conditions; and if yes, stopping optimization of the DMPGA, and using values of the optimal individuals as initial weights of the fully convolutional genetic neural network for the infant brain record images; or otherwise, replacing poor individuals in each population successively with individuals ranked according to the fitness in an elite population for re-initialization, and then the process returning to Step 2.4.

As a further preferred solution of the fully convolutional genetic neural network method for segmentation of infant brain record images of the present disclosure, the forward propagation calculation model of the fully convolutional genetic neural network in step 3 includes a convolutional layer cony, a pooling layer max_pool, and a deconvolution layer deconv:

Step 3.1. inputting the preprocessed infant brain record images, and subjecting the images to convolution cony with a 3×3 convolution kernel and max-pooling max_pool with a 2×2 pooling kernel for five times, so that the images are reduced by a factor of 2, 4, 8, 16, and 32 successively;

Step 3.2. extracting feature address information featuremap during the third and fourth convolution conv$_3$ and conv$_4$ and max-pooling max_pool$_3$ and max_pool$_4$ operations, and performing a weighting operation Q on the weight of the address information, where the calculation is shown by the following formula (7):

$$q' = q(\text{featuremap}) \oplus Q \quad (7)$$

q(featuremap) denoting a value of the feature address information of the infant brain record images, q' denoting a weighted value of the feature address information featuremap, and Q denoting a weighted value after optimization of the DMPGA;

Step 3.3. after the five convolution and pooling operations, designing three deconvolution layers deconv with a 7×7 deconvolution kernel, and initializing the deconvolution weight by using optimal individual parameters obtained based on the DMPGA; and then performing deconvolution for the fifth convolution and pooling result, where the calculation of the deconvolution size ks is shown by the following formula (8):

$$ks = w' + 2 \times \text{padding} - \text{stride} \times (w-1) \quad (8)$$

w denoting the side length of the infant brain record image input in deconvolution, w' denoting the side length of an output infant brain record feature image, stride denoting the stride length of a stroke of the deconvolution kernel, and padding denoting the padding value of a data matrix boundary of the infant brain record images;

where this method can magnify the infant brain record feature image twice by means of upsampling, and the magnified image is integrated with the infant brain record feature image obtained after the fourth pooling and weighting operation, thus implementing superposition pixel by pixel;

Step 3.4. performing deconvolution to magnify the combined infant brain record feature image twice, and then integrating the magnified image with a weighted feature image obtained after the third pooling operation, that is, superposing the images pixel by pixel, to obtain an infant brain record feature image reduced by a factor of 8; and then, performing deconvolution deconv3 for the obtained imaged for the third time to magnify the image eight times, thus finally obtaining an image with the same size as the original infant brain record image; and Step 3.5. determining a result of the pixel-by-pixel classification probability of the infant brain record images by means of the softmax function, and making judgment by using a threshold t, to generate a final result y_true.

Compared to the prior art, the present disclosure has the following technical effects:

1. High efficiency: By means of the DMPGA based on derivative properties of biological inheritance that is designed by the present disclosure, the twin populations are derived from the native populations so that the dimensionality of the target populations raises. The respective crossover probability and mutation probability of all the populations are determined from disjoint intervals, so as to guarantee good solution set search performance. Moreover, the algorithm can still maintain good convergence and population diversity during improvement of the dimensionality of the target populations and the solution set search performance. The distribution of solution sets obtained by means of the DMPGA is more uniform, and better convergence and diversity can be achieved, thus efficiently solving the weight optimization problem of the fully convolutional neural network.

2. High segmentation accuracy: The fully convolutional genetic neural network designed by the present disclosure uses the distinguishing features of the infant brain record images optimized by means of the DMPGA to improve a network input, which overcomes the disadvantages of the conventional fully convolutional neural network only using the grayscale information as the features, thus enabling faster network convergence. Further, in the network deconvolution layer, a weighting operation is performed for the feature information recorded by the convolutional pooling layer, to enhance feature signals, so that the features are well retained, thus dealing with the problem of a low resolution of the infant brain record images to a certain extent. The present disclosure can further improve the segmentation efficiency of the infant brain record images, and is of great significance to the early and correct diagnosis of infant encephalopathy and rehabilitation of infants with the encephalopathy.

DETAILED DESCRIPTION OF THE EMBODIMENTS

The present disclosure is further described in detail below with reference to the accompanying drawings.

Figure 1:
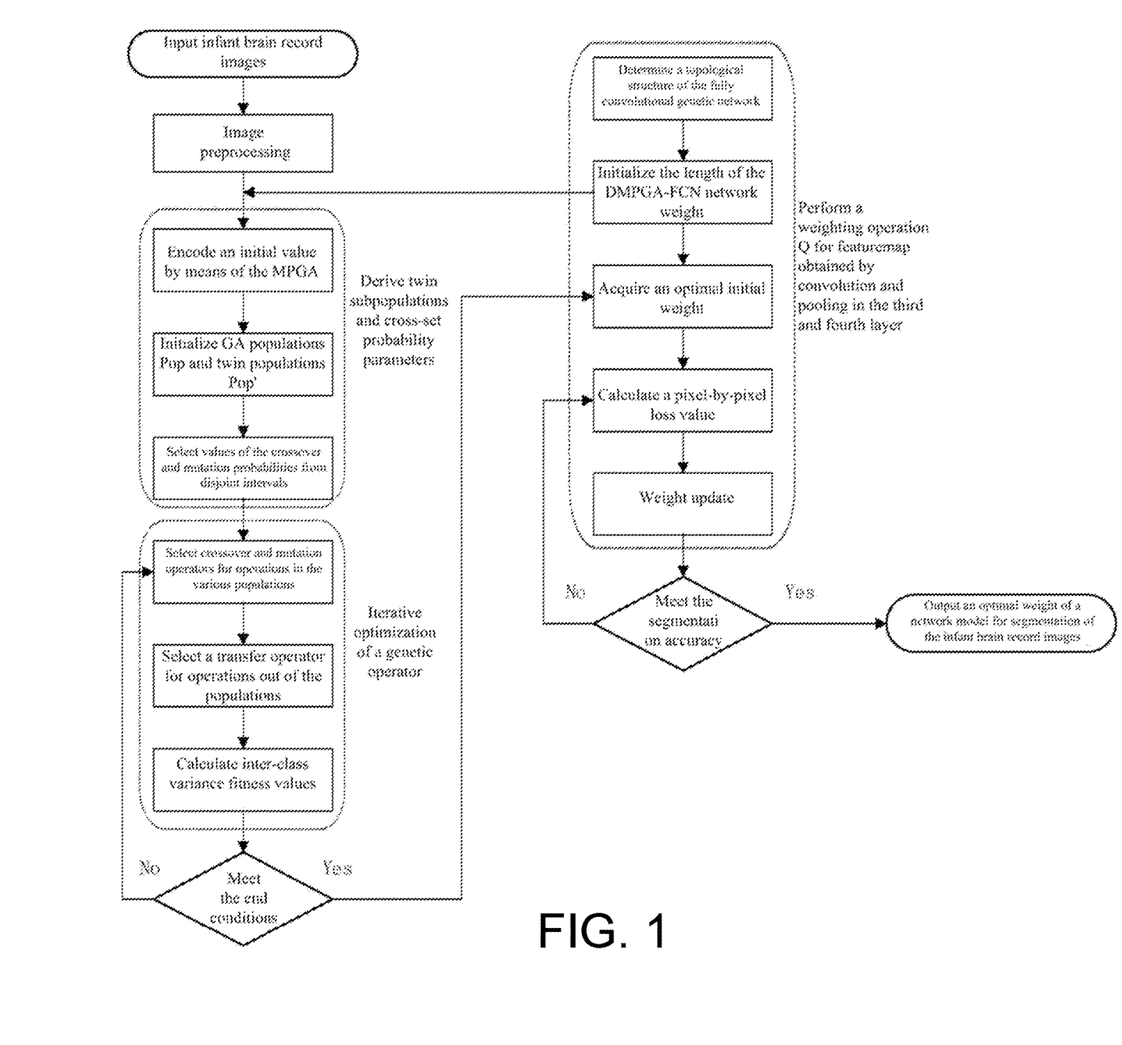
FIG. 1 is an overall flowchart of the present disclosure.
Figure 2:
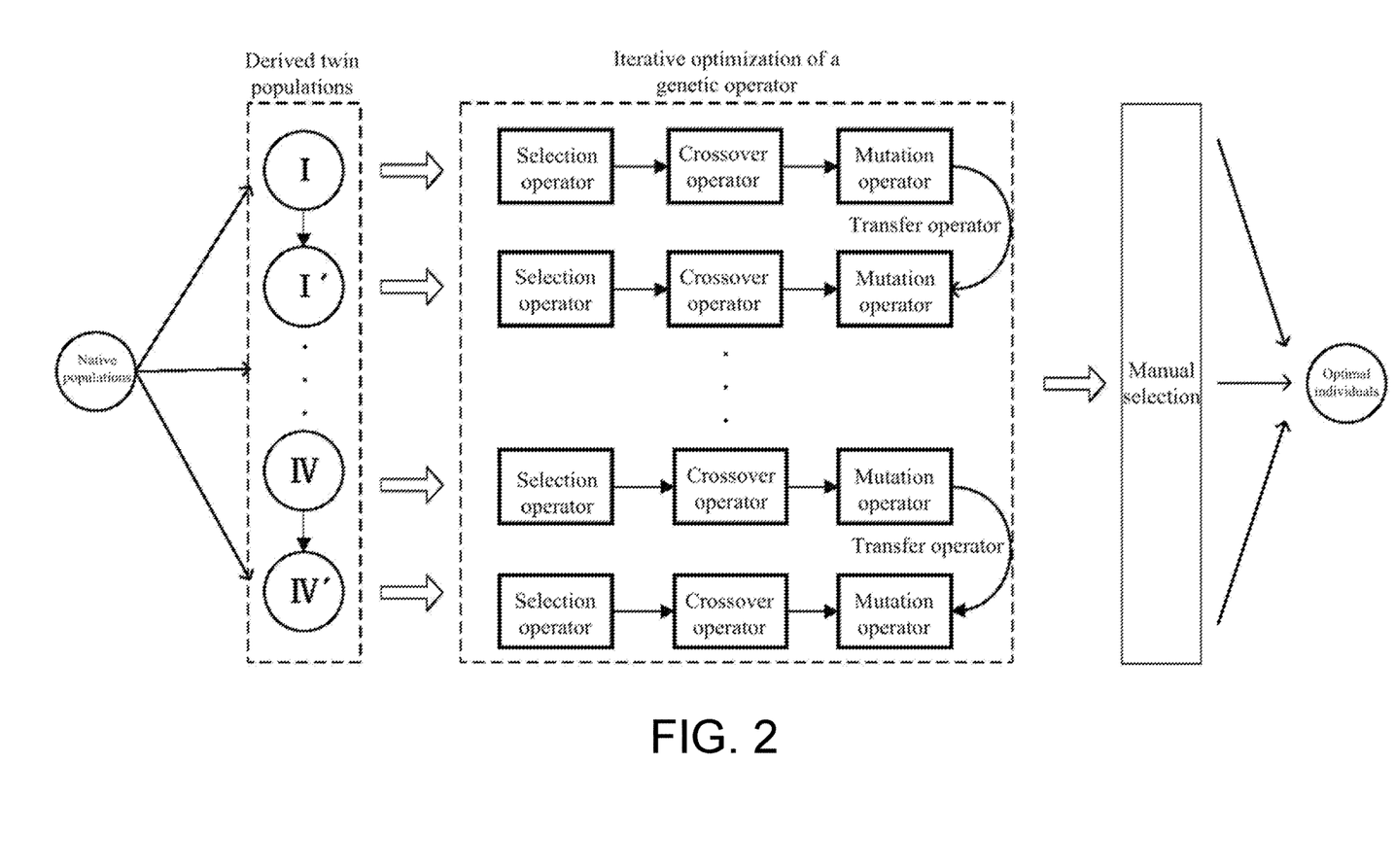
FIG. 2 is a flowchart of a DMPGA for DMPGA-FCN weight optimization in the present disclosure.
Figure 3:
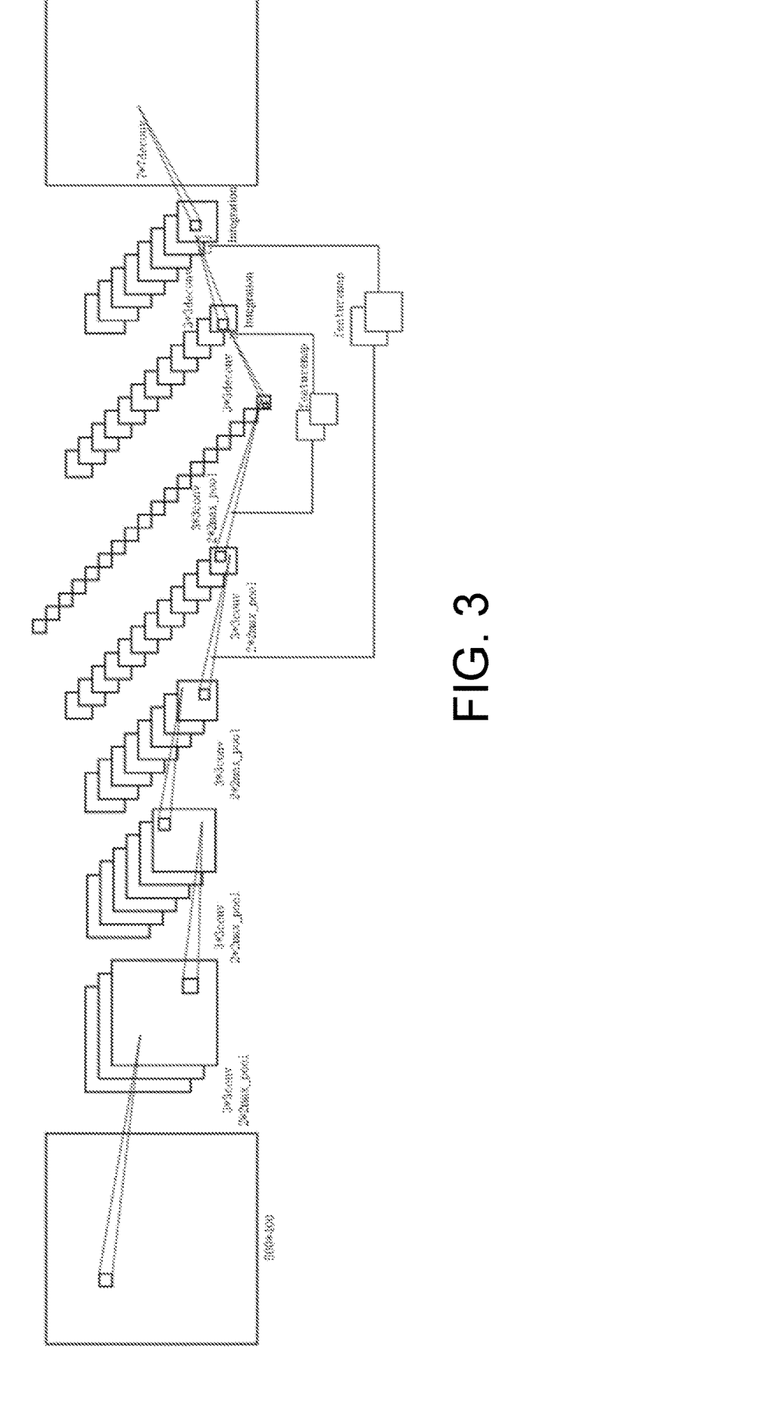
FIG. 3 is a structural diagram of a fully convolutional genetic network of the present disclosure.

As shown in FIGS. 1, 2, and 3, a fully convolutional genetic neural network method for segmentation of infant brain record images is provided, which specifically includes the following steps:

The specific steps of the fully convolutional genetic neural network method for segmentation of infant brain record images are as follows:

Step 1. Standard segmented images of the infant brain record images are input, and grayscale processing and enhancement processing are performed for the infant brain record images. Then, the standard segmented infant brain record images are labeled by using an image labeling tool Image Labeler, where a training set is $X=(x_1, x_2, \ldots, x_n)$, $n=1, 2, 3, \ldots$; and a label set is $B=(b_1, b_2, \ldots, b_n)$, $n=1, 2, 3, \ldots$; and true values y_true of the labels corresponding to the infant brain record images are stored.

Step 2. Bilinear interpolation initialization f(i, j) is performed for weight parameters of the fully convolutional genetic neural network used for the infant brain record images, where specific calculation is shown by the following formula (1):

$$f(i,j)=w_1 \times p_1 + w_2 \times p_2 + w_3 \times p_3 + w_4 \times p_4 \quad (1)$$

where $p_i$ denotes the nearest four pixel points, $i=1, 2, 3, 4$; and $w_j$ denotes a corresponding weight of each point, $j=1, 2, 3, 4$. m individuals with a coding length of L are generated by means of binary coding, where calculation of L is shown by the following formula (2):

$$L = F \times F \times D \times N \quad (2)$$

where L is a coding length of the genetic individual, F is the size of a convolution kernel, N is the number of the convolution kernels, and D is the depth of a convolutional layer.

The individuals are randomly assigned to a native sub-population Pop, and a twin population Pop' is derived to generate an initial genetic evolution population.

Values of a crossover probability pc and a mutation probability pm of the native population and its twin population are both selected from disjoint intervals (0,1/2) and [1/2,1). A feasible domain is searched for optimal individuals by using a genetic operator, and calculation is conducted by using the inter-class variance function as the fitness function f, where the calculation is shown by the following formula (3):

$$f = n_1 n_2 (G_{1k} - G_{2k})^2, \ k=1,2,3, \ldots n, \quad (3)$$

where $n_1$ and $n_2$ respectively denote the numbers of the pixel points of the two foreground and background types in the infant brain record images, $G_{1k}$ denotes the gray level of the kth pixel point of the first type, and $G_{2k}$ denotes the gray level of the kth pixel point of the second type.

The superiority of the individuals is criticized according to the fitness function f and the individuals in the population are constantly updated, till the genetic algorithm meets convergence conditions, to obtain globally optimal individuals fa; and all the individuals in fa are used as initial weights of the fully convolutional genetic neural network for the infant brain record images.

Step 2 includes the following steps:

Step 2.1. A forward propagation calculation model of the fully convolutional genetic neural network is established; a few infant brain record images are randomly selected from the training set of the standard segmented infant brain record images as reference images, and the images left in the training set are used as a validation set; and training and validation are repeatedly performed by means of cross validation.

Step 2.2. The number m of the genetic individuals is determined, and bilinear interpolation initialization f(i, j) is performed for the weight parameters of the fully convolutional genetic neural network, where specific calculation is shown by the formula (1); and m individuals with a coding length of L are generated by means of binary coding, where calculation of L is shown by the formula (2).

Step 2.3. All the individuals are randomly grouped into native populations Pop, and corresponding twin populations Pop' are derived, to finally form initial genetic evolution populations.

Step 2.4. Values of a crossover probability $p_c$ and a mutation probability $p_m$ of each pair of the native population Pop and its twin population Pop' are selected from disjoint intervals, that is, the respective crossover probability $p_c$ and mutation probability $p_m$ of all the populations are randomly generated within (0,1/2) and [1/2,1) respectively.

Step 2.5. Three optimal individuals are selected with a certain probability from the original population to the new population by using a selection operator; and then any two chromosomes are selected from the population by using a crossover operator, and a gene locus is randomly selected according to the probability $p_c$ in exchange with each site in the chromosomes. The calculation is shown by the following formula (4):

$$a_{mi}=a_{mi}\times(1-p_c)+a_{mi}\times p_c;\ a_{ni}=a_{ni}\times(1-p_c)+a_{ni}\times p_c \quad (4)$$

where $a_{mi}$ denotes the ith site of the mth chromosome, $a_{ni}$ denotes the ith site of the nth chromosome, and $p_c$ is the crossover probability.

Afterwards, an individual is randomly selected from the population by using a mutation operator, and a gene locus is selected from the individual with the probability $p_m$ for mutation, to generate a more superior individual. The calculation is shown by the following formula (5):

$$a_{mn}=a_{mn}+(a_{mn}-a_{max})\times p_m \quad (5)$$

where $a_{mn}$ denotes the nth site of the mth chromosome, $a_{max}$ denotes the upper genetic boundary, and $p_m$ is the mutation probability.

Step 2.6. The worst individuals in the immigrant population are replaced with the optimal individuals in the emigrant population among the various populations by using a transfer operator, and then calculation is conducted by using the inter-class variance function as the fitness function f, to criticize the superiority of the individuals, where the calculation is shown by the formula (3).

Step 2.7. It is determined whether a DMPGA meets convergence conditions; and if yes, optimization of the DMPGA is stopped, and values of the optimal individuals are used as initial weights of the fully convolutional genetic neural network for the infant brain record images; or otherwise, poor individuals in each population are replaced successively with individuals ranked according to the fitness in an elite population for re-initialization, and then the process returns to Step 2.4.

Step 3. The jth standard segmented infant brain record image in the training set is input to the forward propagation calculation model of the fully convolutional genetic neural network, and is subjected to convolution cony, pooling pool, and deconvolution deconv calculation through multiple layers; and finally, statistical calculation of the pixel-by-pixel classification probability is conducted, to output a predicted value matrix y_predict in the jth operation.

The forward propagation calculation model of the fully convolutional genetic neural network in step 3 includes a convolutional layer cony, a pooling layer max_pool, and a deconvolution layer deconv.

Step 3.1. The preprocessed infant brain record images are input, and subjected to convolution cony with a 3×3 convolution kernel and max-pooling max_pool with a 2×2 pooling kernel for five times, so that the images are reduced by a factor of 2, 4, 8, 16, and 32 successively.

Step 3.2. Feature address information featuremap is extracted during the third and fourth convolution $conv_3$ and $conv_4$ and max-pooling $max\_pool_3$ and $max\_pool_4$ operations, and a weighting operation Q is performed on the weight of the address information, where the calculation is shown by the following formula (6):

$$q'=q(\text{featuremap})\oplus Q \quad (6)$$

where q(featuremap) denotes a value of the feature address information of the infant brain record images, q' denotes a weighted value of the feature address information featuremap, and Q denotes a weighted value after optimization of the DMPGA.

Step 3.3. After the five convolution and pooling operations, three deconvolution layers deconv with a 7×7 deconvolution kernel are designed, and the deconvolution weight is initialized by using optimal individual parameters obtained based on the DMPGA; and then deconvolution is performed for the fifth convolution and pooling result, where the calculation of the deconvolution size ks is shown by the following formula (7):

$$ks=w'+2\times padding-stride\times(w-1) \quad (7)$$

where w denotes the side length of the infant brain record image input in deconvolution, w' denotes the side length of an output infant brain record feature image, stride denotes the stride length of a stroke of the deconvolution kernel, and padding denotes the padding value of a data matrix boundary of the infant brain record images.

This method can magnify the infant brain record feature image twice by means of upsampling, and the magnified image is integrated with the infant brain record feature image obtained after the fourth pooling and weighting operation, thus implementing superposition pixel by pixel.

Step 3.4. Deconvolution is performed to magnify the combined infant brain record feature image twice, and then the magnified image is integrated with a weighted feature image obtained after the third pooling operation, that is, the images are superposed pixel by pixel, to obtain an infant brain record feature image reduced by a factor of 8. Then, deconvolution deconv3 is performed for the obtained imaged for the third time to magnify the image eight times, thus finally obtaining an image with the same size as the original infant brain record image.

Step 3.5. A result of the pixel-by-pixel classification probability of the infant brain record images is determined by means of the softmax function, and judgment is made by using a threshold t, to generate a final result y_true.

Step 4. Softmax calculation softmax (y_predict) is performed by using a true value y_true$_{ij}$ and a predicted value y_predict$_{ij}$ in the mth operation, and a pixel-by-pixel cross-entropy loss of the infant brain record images is calculated, to obtain a loss value loss$_m$ in the mth operation, where the calculation is shown by the following formula (8):

$$\text{loss}_m = -\Sigma_{class} y\_true_{ij} \log(y\_predict_{ij}) \quad (8)$$

where y_true$_{ij}$ denotes a predicted value in the ith row and jth column of a pixel-by-pixel classification matrix, y_predict$_{ij}$ denotes a value in the ith row and jth column of the classification matrix of the standard segmented infant brain record images, and class denotes a total number of i×j pixels.

Step 5. Callback of the network weights is performed by returning the loos value and by means of a gradient descent algorithm; and it is determined whether the network reaches end conditions, and if yes, final network weights are used as the final trained weight parameters of the fully convolutional genetic neural network.

Step 6. The final trained weight parameters are introduced into the network to form a fully convolutional genetic neural network model for segmentation of the infant brain record images; then, the infant brain record images are input, and are subjected to convolution cony, max-pooling max_pool, and deconvolution deconv calculation through multiple layers, to output segmented infant brain record images and further output pixel-by-pixel classification matrices y_ture.

By means of the genetic algorithm DMPGA based on derivative properties of biological inheritance that is designed by the present disclosure, the twin populations are derived from the native populations so that the dimensionality of the target populations raises. The respective crossover probability and mutation probability of all the populations are determined from disjoint intervals, so as to guarantee good solution set search performance. Moreover, the algorithm can still maintain good convergence and population diversity during improvement of the dimensionality of the target populations and the solution set search performance. The distribution of solution sets obtained by means of the DMPGA is more uniform, and better convergence and diversity can be achieved, thus efficiently solving the weight optimization problem of the fully convolutional neural network.

The fully convolutional genetic neural network designed by the present disclosure uses the distinguishing features of the infant brain record images optimized by means of the DMPGA to improve a network input, which overcomes the disadvantages of the conventional fully convolutional neural network only using the grayscale information as the features, thus enabling faster network convergence. Further, in the network deconvolution layer, a weighting operation is performed on the feature information recorded by the convolutional pooling layer, to enhance feature signals, so that the features are well retained, thus dealing with the problem of a low resolution of the infant brain record images to a certain extent. The method can further improve the segmentation efficiency of the infant brain record images, and is of great significance to the early and correct diagnosis of infant encephalopathy and rehabilitation of infants with the encephalopathy.

The specific embodiments described above further describe the purpose, technical solutions, and beneficial effects of the present disclosure in further detail. It should be understood that the above descriptions are only specific embodiments of the present disclosure, and are not intended to limit the scope of the present disclosure. The equivalent changes and modifications made by any person skilled in the art without departing from the concept and principle of the present disclosure shall all fall within the protection scope of the present disclosure.

What is claimed is:

1. A fully convolutional genetic neural network method for a segmentation of infant brain record images, comprising the following steps:

step 1. inputting standard segmented images of the infant brain record images, and performing a grayscale processing and an enhancement processing for the infant brain record images; then, labeling standard segmented infant brain record images by using an image labeling tool Image Labeler, wherein a training set is X=(x$_1$, x$_2$, ..., x$_n$), n=1, 2, 3, ... ; and a label set is B=(b$_1$, b$_2$, ..., b$_n$), n=1, 2, 3, ... ; and storing true values y_true of labels corresponding to the infant brain record images;

step 2. performing a bilinear interpolation initialization f (i, j) for weight parameters of a fully convolutional genetic neural network used for the infant brain record images, wherein specific calculation is shown by the following formula (1):

$$f(i,j) = w_1 \times p_1 + w_2 \times p_2 + w_3 \times p_3 + w_4 \times p_4 \quad (1)$$

p$_i$ denoting nearest four pixel points, i=1, 2, 3, 4; and w$_j$ denoting a corresponding weight of each point, j=1, 2, 3, 4; generating m individuals with a coding length of L by means of binary coding, wherein calculation of L is shown by the following formula (2):

$$L = F \times F \times D \times N \quad (2)$$

L being the coding length of genetic individuals, F being a size of convolution kernels, N being a number of the convolution kernels, and D being a depth of a convolutional layer;

randomly assigning individuals to a native population Pop, and deriving twin populations Pop' to generate an initial genetic evolution population, wherein values of a crossover probability p$_c$ and a mutation probability p$_m$ of the native population and its the twin population are both selected from disjoint intervals (0,1/2) and [1/2,1); searching a feasible domain for optimal individuals by using a genetic operator, and conducting calculation by using an inter-class variance function as a fitness function f, wherein the calculation is shown by the following formula (3):

$$f = n_1 n_2 (G_{1k} - G_{2k})^2, \ k=1,2,3,\ldots n, \quad (3)$$

n$_1$ and n$_2$ respectively denoting numbers of pixel points of two foreground and background types in the infant brain record images, G$_{1k}$ denoting a gray level of a kth pixel point of a first type, and G$_{2k}$ denoting the gray level of the kth pixel point of a second type;

criticizing a superiority of the individuals according to the fitness function f and constantly updating the individuals in populations, till a genetic algorithm meets convergence conditions, to obtain a globally optimal individuals fa; and using all the individuals in fa as initial weights of the fully convolutional genetic neural network for the infant brain record images;

step 3. inputting a jth standard segmented infant brain record image in the training set to a forward propagation calculation model of the fully convolutional genetic neural network, and subjecting it to a convolution cony, a pooling pool, and a deconvolution deconv calculation through multiple layers; and finally, conducting a statistical calculation of a pixel-by-pixel classification probability, to output a predicted value matrix y_predict in a jth operation;

step 4. conducting a softmax calculation softmax (y_predict) by using a true value y_true$_{ij}$ and a predicted value y_predict$_{ij}$ in a mth operation, and calculating a pixel-by-pixel cross-entropy loss of the infant brain record images, to obtain a loss value loss$_m$ in the mth operation, wherein the calculation is shown by the following formula (4):

$$loss_m = -\Sigma_{class} y\_true_{ij} \log(y\_predict_{ij}) \quad (4)$$

y_true$_{ij}$ denoting a predicted value in a ith row and a jth column of a pixel-by-pixel classification matrix, y_predict$_{ij}$ denoting a value in the ith row and the jth column of a classification matrix of the standard segmented infant brain record images, and class denoting a total number of i×j pixels;

step 5. performing a callback of network weights by returning loos value and by means of a gradient descent algorithm, determining whether network reaches end conditions, and if yes, using final network weights as final trained weight parameters of the fully convolutional genetic neural network; and step 6. introducing the final trained weight parameters into the fully convolutional genetic neural network to form a fully convolutional genetic neural network model for the segmentation of the infant brain record images; then, inputting the infant brain record images, and subjecting the infant brain record images to the convolution cony, max-pooling max_pool, and the deconvolution deconv calculation through the multiple layers, to output segmented infant brain record images and further output pixel-by-pixel classification matrices y_ture.

2. The fully convolutional genetic neural network method for the segmentation of the infant brain record images according to claim 1, wherein the Step 2 comprises the following steps:

step 2.1. establishing the forward propagation calculation model of the fully convolutional genetic neural network; randomly selecting a few of the infant brain record images from the training set of the standard segmented infant brain record images as reference images, and using the standard segmented infant brain record images, which are the rest of the standard segmented infant brain record images in the training set, as a validation set; and repeatedly performing a training and a validation by means of a cross validation;

step 2.2. determining a number m of the genetic individuals, and performing the bilinear interpolation initialization f(i, j) for the weight parameters of the fully convolutional genetic neural network, wherein the calculation is shown by the formula (1); and generating the m individuals with the coding length of L by means of binary coding, wherein calculation of L is shown by the formula (2);

step 2.3. randomly grouping all the individuals into native populations Pop, and deriving twin populations Pop', to finally form the initial genetic evolution population;

step 2.4. selecting the values of the crossover probability p$_c$ and the mutation probability p$_m$ of each pair of the native population Pop and its the twin population Pop' from the disjoint intervals, that is, randomly generating the crossover probability p$_c$ that is respective, and the mutation probability p$_m$ of all the populations within (0,1/2) and [1/2,1) respectively;

step 2.5. selecting three optimal individuals with a certain probability from an original population to a new population by using a selection operator; and then selecting any two chromosomes from the populations by using a crossover operator, and randomly selecting a gene locus according to a probability of p$_c$ in exchange with each site in the chromosomes, wherein the calculation is shown by the following formula (5):

$$a_{mi} = a_{mi} \times (1-p_c) + a_{mi} \times p_c; \quad a_{ni} = a_{ni} \times (1-p_c) + a_{ni} \times p_c \quad (5)$$

a$_{mi}$ denoting an ith site of a mth chromosome, a$_{ni}$ denoting the ith site of a nth chromosome, and p$_c$ being the crossover probability; and afterwards, randomly selecting an individual from the populations by using a mutation operator, and selecting one of the gene locus from the individual with a probability of p$_m$ for mutation, to generate a more superior individual, wherein the calculation is shown by the following formula (6):

$$a_{mn} = a_{mn} + (a_{mn} - a_{max}) \times p_m \quad (6)$$

a$_{mn}$ denoting a nth site of the mth chromosome, a$_{max}$ denoting an upper genetic boundary, and p$_m$ being the mutation probability;

step 2.6. replacing worst individuals in an immigrant population with the optimal individuals in an emigrant population among each of the populations by using a transfer operator, and then conducting calculation by using the inter-class variance function as the fitness function f, to criticize the superiority of the individuals, wherein the calculation is shown by the formula (3); and step 2.7. determining whether a derived multi-population genetic algorithm (DMPGA) meets the convergence conditions; and if yes, stopping optimization of the DMPGA, and using values of the optimal individuals as the initial weights of the fully convolutional genetic neural network for the infant brain record images; or otherwise, replacing poor individuals in each the populations successively with the individuals ranked according to a fitness in an elite population for re-initialization, and then the process returning to Step 2.4.

3. The fully convolutional genetic neural network method for the segmentation of the infant brain record images according to claim 1, wherein the forward propagation calculation model of the fully convolutional genetic neural network in the step 3 comprises a convolutional layer cony, a pooling layer max_pool, and a deconvolution layer deconv:

step 3.1. inputting the infant brain record images, which are preprocessed, and subjecting the infant brain record images, which are preprocessed, to the convolution cony with a 3×3 convolution kernel and a max-pooling max_pool with a 2×2 pooling kernel for five times, so that the infant brain record images, which are preprocessed, are reduced by a factor of 2, 4, 8, 16, and 32 successively;

step 3.2. extracting a feature address information feature-map during a third and a fourth convolution conv$_3$ and conv$_4$ and a max-pooling max_pool$_3$ and max_pool$_4$ operations, and performing a weighting operation Q on a weight of an address information, wherein the calculation is shown by the following formula (7):

$$q' = q(\text{featuremap}) \oplus Q \quad (7)$$

q(featuremap) denoting a value of a feature address information of the infant brain record images, q' denoting a value of the feature address information featuremap after weighting, and Q denoting a weighted value after optimization of the DMPGA;

step 3.3. after a five convolution and pooling operations, designing three deconvolution layers deconv with a 7×7 deconvolution kernel, and initializing a deconvolution weight by using optimal individual parameters obtained based on the DMPGA; and then performing a deconvolution for a fifth convolution and pooling result, wherein the calculation of a deconvolution size ks is shown by the following formula (8):

$$ks = w' + 2 \times padding - stride \times (w-1) \tag{8}$$

w denoting a side length of the infant brain record images input in deconvolution, w' denoting a side length of an output infant brain record feature image, stride denoting a stride length of a stroke of a deconvolution kernel, and padding denoting a padding value of a data matrix boundary of the infant brain record images;

wherein this method is able to magnify an infant brain record feature image twice by means of upsampling, and a magnified image is integrated with the infant brain record feature image obtained after a fourth pooling and weighting operation, thus implementing superposition pixel by pixel;

step 3.4. performing the deconvolution to magnify the infant brain record feature image that is combined twice, and then integrating the magnified image with a weighted feature image obtained after a third pooling operation, that is, superposing the images pixel by pixel, to obtain an infant brain record feature image reduced by a factor of 8; and then, performing a deconvolution $deconv_3$ for a obtained image for the third time to magnify an image eight times, thus finally obtaining an image with the same size as an original infant brain record image; and step 3.5. determining a result of the pixel-by-pixel classification probability of the infant brain record images by means of a softmax function, and making judgment by using a threshold t, to generate a final result y_true.

* * * * *